United States Patent [19]
Allen et al.

[11] Patent Number: 5,919,790
[45] Date of Patent: Jul. 6, 1999

[54] HYDROXAMATE INHIBITORS OF INTERLEUKIN-1β CONVERTING ENZYME

[75] Inventors: Hamish John Allen, Shrewsbury; Kenneth Dale Brady, Worcester, both of Mass.; Bradley William Caprathe, Livonia, Mich.; Paul Galatsis, Ann Arbor, Mich.; John Lodge Gilmore, Ann Arbor, Mich.; Sheryl Jeanne Hays, Ann Arbor, Mich.; Robert Vincent Talanian, Harvard, Mass.; Nigel Walker, Dossenheim, Germany; Joseph Scott Warmus, Ann Arbor, Mich.

[73] Assignees: Warner-Lambert Company, Morris Plains, N.J.; BASF Aktiengesellsschaft, Ludwigshafen, Germany

[21] Appl. No.: 08/942,605

[22] Filed: Oct. 2, 1997

Related U.S. Application Data

[60] Provisional application No. 60/028,324, Oct. 11, 1996.

[51] Int. Cl.⁶ ............... A61K 31/405; A61K 31/44; C07C 259/08; C07C 229/32; C07D 209/34; C07D 209/46; C07D 209/48; C07D 221/20

[52] U.S. Cl. ............... 514/278; 514/412; 514/416; 514/417; 514/418; 514/424; 514/425; 546/18; 546/122; 546/139; 546/249; 548/472; 548/475; 548/486; 548/512; 548/514; 548/530; 548/300.1; 548/146; 560/312; 562/444; 544/242; 549/29; 549/49; 549/434

[58] Field of Search ............... 514/278, 412, 514/416, 417, 418, 424, 425; 546/18; 548/475, 486, 472, 514, 512

[56] References Cited

U.S. PATENT DOCUMENTS 5,656,627  8/1997  Bemis et al. ............... 514/221

FOREIGN PATENT DOCUMENTS

| | | |
|---|---|---|
| 644198 | 3/1995 | European Pat. Off. . |
| 95/26958 | 10/1995 | WIPO . |
| 95/33751 | 12/1995 | WIPO . |
| 95/35308 | 12/1995 | WIPO . |
| 97/22619 | 6/1997 | WIPO . |

*Primary Examiner*—Johann Richter
*Assistant Examiner*—Jane C. Osweeki
*Attorney, Agent, or Firm*—Todd M. Crissey

[57] ABSTRACT

The present invention relates to compounds that are inhibitors of interleukin-1β converting enzyme that have the Formula II

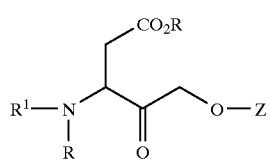

This invention also relates to a method of treatment of stroke, inflammatory diseases, septic shock, reperfusion injury, Alzheimer's disease, shigellosis, and to a pharmaceutically acceptable composition that contains a compound that is an inhibitor of interleukin-1β converting enzyme.

16 Claims, No Drawings

HYDROXAMATE INHIBITORS OF INTERLEUKIN-1β CONVERTING ENZYME

This application claims the benefit of U.S. Provisional application Ser. No. 60/028,324 filed Oct. 11, 1996.

FIELD OF THE INVENTION

This invention relates to compounds that are inhibitors of interleukin-1β converting enzyme. This invention also relates to a method of treatment of stroke, inflammatory diseases, septic shock, reperfusion injury, Alzheimer's disease, shigellosis, and to a pharmaceutically acceptable composition that contains a compound that is an inhibitor of interleukin-1β converting enzyme.

BACKGROUND OF THE INVENTION

The compounds of the present invention are inhibitors of interleukin-1β converting enzyme (ICE) and are useful in treating diseases in which interleukin-1 plays a role.

ICE acts on pro-interleukin-1β (pro-IL-1β) to produce interleukin-1β (IL-1β), which is an inflammatory cytokine. Several diseases are associated with interleukin-1 activity. Examples of diseases in which interleukin-1 is involved include, but are not limited to, inflammatory diseases such as rheumatoid arthritis and inflammatory bowel disease, and neuroinflamatory disorders such as stroke. Other diseases include septic shock, reperfusion injury, Alzheimer's disease, and shigellosis.

Agents that modulate IL-1β activity have been shown to have beneficial in vivo effects. For example, compounds that are interleukin-1 receptor antagonists have been shown to inhibit ischemic and excitotoxic damage in rat brains. See, for example, Relton J. K., et al., *Brain Research Bulletin*, 1992;29:243–246. Additionally, ICE inhibitors were shown to reduce inflammation and pyrexia in rats. See Elford P. R., et al., *British Journal of Pharmacology*, 1995;115:601–606.

The compounds of the present invention are also inhibitors of other cysteine proteases in the ICE family. Many of these proteases have only recently been described in the literature. While the nomenclature is still unresolved, the following proteases are representative members of this class of enzymes; Ich-2 (also called Tx or ICErel-II), ICErel-III, Ich-I (also called Nedd-2), CPP-32 (also called apopain and yama), Mch-2, Mch-3 (also called ICE-lap3, CMH-1), and Ced-3. See Henkart P. A., *Immunity*, 1996;4:195–201. It is recognized that members of this enzyme family play key biological roles in both inflammation and apoptosis (programmed cell death). See Thornberry N. A., et al., *Perspectives in Drulg Discovery and Design*, 1994;2:389–399.

In addition to its effects on IL-1β production, ICE has been shown to play a role in the production of the inflammatory mediator interferon-γ (Guyur, et al., *Nature*, 1997;386(6625):619–623). ICE processes the inactive proform of interferon-γ inducing factor (IGIF; Interleukin-18) to active IGIF, a protein which induces production of interferon-γ by T-cells and natural killer cells. Interferon-γ has been implicated in the pathogenesis of diseases such as inflammatory disorders and septic shock. Therefore, ICE inhibitors would be expected to have beneficial effects in such disease states by effects on interferon-γ.

Recently, the nomenclature of these cysteine proteases in the ICE family (also known as Caspases with ICE being known as Caspase-1) has been further defined. The following proteases are representative members of this class of enzymes using the nomenclature described in Alnemri, et al., *Cell*, 1996;87:171: Caspase-2 (also known as Ich-1); Caspase-3 (also known as CPP32, yama, and apopain); Caspase-4 (also known as TX, Ich-2, and ICE rel-II); Caspase-5 (also known as ICE rel-III); Caspase-6 (also known as Mch2); Caspase-7 (also known as Mch3); Caspase-8 (also known as FLICE and Mch5); Caspase-9 (also known as ICE-LAP6 and Mch6); Caspase-10 (also known as Mch4).

SUMMARY OF THE INVENTION

The present invention provides compounds having the Formula I

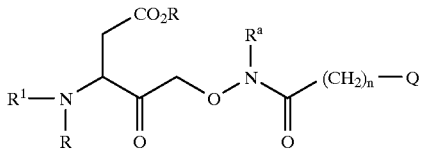

wherein $R^1$ is

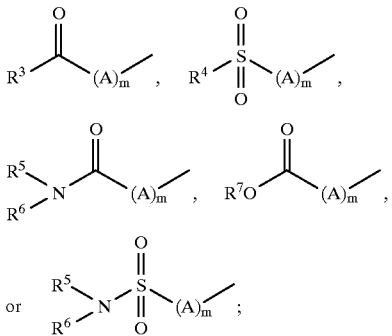

each R is independently hydrogen or $C_1$–$C_6$alkyl;

$R^3$ is hydrogen, $C_1$–$C_6$alkyl, —$(CH_2)_n$aryl, —$(CH_2)_n$heteroaryl, —$(CH_2)_p$-X-aryl, or —$(CH_2)_p$-X-heteroaryl;

$R^4$ is $C_1$–$C_6$alkyl, —$(CH_2)_n$aryl, —$(CH_2)_n$heteroaryl, —$(CH_2)_j$-X-aryl, or —$(CH_2)_j$-X-heteroaryl;

$R^5$ and $R^6$ are each independently hydrogen, $C_1$–$C_6$alkyl, —$(CH_2)_n$aryl, —$(CH_2)_n$heteroaryl, —$(CH_2)_j$-X-aryl, or —$(CH_2)_j$-X-heteroaryl;

$R^7$ is $C_1$–$C_6$alkyl, —$(CH_2)_p$aryl, —$(CH_2)_p$ heteroaryl, —$(CH_2)_j$-X-aryl, or —$(CH_2)_j$-X-heteroaryl;

each n is independently 0 to 6;

each p is independently 1 to 6;

each j is independently 2 to 6;

each m is 0 to 2;

A is alanine, valine, serine, threonine, glutamic acid, lysine, arginine, histidine, glutamine, or alpha amino butyric acid;

$R^a$ is hydrogen, $C_1$–$C_6$alkyl, or —$(CH_2)_n$phenyl; X is O or S; and

Q is $C_1$–$C_6$alkyl, —$(CH_2)_n$aryl, —$(CH_2)_n$heteroaryl, and the pharmaceutically acceptable salts, esters, amides, and prodrugs thereof.

In one embodiment of the compounds of Formula I, each R is hydrogen.

In another embodiment of the compounds of Formula I, $R^1$ is and m is 0.

In another embodiment of the compounds of Formula I, $R^1$ is

[structure: $R^7O-C(=O)-(A)_m-$]

m is 0, and $R^7$ is $-(CH_2)_n$aryl.

In another embodiment of the compounds of Formula I, Q is $-(CH_2)_n$phenyl or $-(CH_2)_n$naphthyl.

In another embodiment of the compounds of Formula I, $R^a$ is hydrogen or methyl.

In another embodiment of the compounds of Formula I, Q is $-CH_2$-phenyl, $-CH_2$-naphthyl, $-CH_2CH_2$-phenyl, or $-CH_2CH_2$-naphthyl.

In a preferred embodiment, the present invention provides the compounds.

In another aspect, the present invention provides compounds having the Formula II

[structure II: $R^1-N(R)-CH(CH_2CO_2R)-C(=O)-CH_2-O-Z$]

wherein Z is

[structures with g substituents]

each g is independently hydrogen, $C_1-C_6$alkyl, $C_1-C_6$alkoxy, $-(CH_2)_nCO_2R$, $-(CH_2)_n$aryl, -aryl, $-(CH_2)_n$heteroaryl, or -heteroaryl;

U is O or $CH_2$;

$R^1$ is

[structures: $R^3-C(=O)-(A)_m-$, $R^4-S(=O)_2-(A)_m-$, $R^5R^6N-C(=O)-(A)_m-$, $R^7O-C(=O)-(A)_m-$, or $R^5R^6N-S(=O)_2-(A)_m-$];

each R is independently hydrogen or $C_1-C_6$alkyl;

$R^3$ is hydrogen, $C_1-C_6$alkyl, $-(CH_2)_n$aryl, $-(CH_2)_n$heteroaryl, $-(CH_2)_p$-X-aryl, or $-(CH_2)_p$-X-heteroaryl;

$R^4$ is $C_1-C_6$alkyl, $-(CH_2)_n$aryl, $-(CH_2)_n$heteroaryl, $-(CH_2)_j$-X-aryl, or $-(CH_2)_j$-X-heteroaryl;

$R^5$ and $R^6$ are each independently hydrogen, $C_1-C_6$alkyl, $-(CH_2)_n$aryl, $-(CH_2)_n$heteroaryl, $-(CH_2)_j$-X-aryl, or $-(CH_2)_j$-X-heteroaryl;

$R^7$ is $C_1-C_6$alkyl, $-(CH_2)_p$aryl, $-(CH_2)_p$heteroaryl, $-(CH_2)_j$-X-aryl, or $-(CH_2)_j$-X-heteroaryl;

each n is independently 0 to 6;

each p is independently 1 to 6;

each j is independently 2 to 6;

each m is 0 to 2;

A is alanine, valine, serine, threonine, glutamic acid, lysine, arginine, histidine, glutamine, or alpha amino butyric acid; and X is O or S, and the pharmaceutically acceptable salts, esters, amides, and prodrugs thereof.

In one embodiment of the compounds of Formula II, Z is

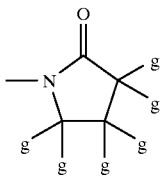

and each g is hydrogen.

In another embodiment of the compounds of Formula II, $R^1$ is

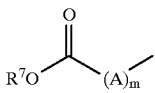

and m is 0

In one embodiment of the compounds of Formula II, $R^1$ is

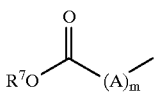

m is 0, and $R^7$ is —$(CH_2)_n$-aryl.

In one embodiment of the compounds of Formula II, $R^7$ is —$(CH_2)_n$-phenyl.

In a preferred embodiment of the compounds of Formula II, Z is

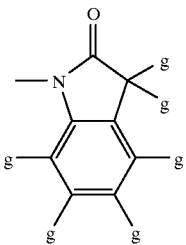

and each g is hydrogen.

In a more preferred embodiment, the present invention provides the compounds
3-Benzyloxycarbonyl-amino-4-oxo-5-phenylacetylaminooxy-pentanoic acid;
3-Benzyloxycarbonylamino-4-oxo-5-(2-oxo-pyrrolidin-1-yloxy)-pentanoic acid;
3-Benzyloxycarbonylamino-5-(3,5-dioxo-10-oxa-4-aza-tricyclo [5.2.1.0$^{2,6}$]dec-8-en-4-yloxy)-4-oxo-pentanoic acid;
3-Benzyloxycarbonylamino-5-(2-oxo-2,3-dihydro-indol-1-yloxy)-4-oxo-pentanoic acid;
3-Benzyloxycarbonylamino-5-(7-methoxycarbonylmethyl-2-oxo-octahydro-indol-1-yloxy)-4-oxo-pentanoic acid;
3-Benzyloxycarbonylamino-4-oxo-5-(2-oxo-octahydro-indol-1-yloxy)-pentanoic acid;
3-[2-(2-Benzyloxycarbonylamino-3-methyl-butyrylamino)-propionylamino]-5-(7-methoxycarbonylmethyl-2-oxo-octahydro-indol-1-yloxy)-4-oxo-pentanoic acid;
3-[2-(2-benzyloxycarbonylamino-3-methyl-butyrylamino)-propionylamino]-4-oxo-5-(2-oxo-2,3-dihydro-indol-1-yloxy)-pentanoic acid;
3-Benzyloxycarbonylamino-5-(2,5-dioxo-pyrrolidin-1-yloxy)-4-oxo-pentanoic acid;
3-Benzyloxycarbonylamino-4-oxo-5-(2,2,3-trimethyl-5-oxo-pyrrolidin-1-yloxy)-pentanoic acid;
3-Benzyloxycarbonylamino-5-(1, 3-dioxo-octahydro-isoindol-2-yloxy)-4-oxo-pentanoic acid;
3-Benzyloxycarbonylamino-5-(1,3-dioxo-1,3-dihydro-isoindol-2-yloxy)-4-oxo-pentanoic acid;
3-Benzyloxycarbonylamino-5-[3-(4-bromo-phenyl)-2,5-dioxo-2,5-dihydro-pyrrol-1-yloxy]-4-oxo-pentanoic acid;
3-Benzyloxycarbonylamino-5-(3,5-dioxo-4-aza-tricyclo [5.2.1.0$^{2,6}$]dec-8-en-4-yloxy)-4-oxo-pentanoic acid;
3-Benzyloxycarbonylamino-5-(2,4-dioxo-3-aza-spiro[5.5] undec-3-yloxy)-4-oxo-pentanoic acid;
5-(2-Biphenyl-4-yl-5-oxo-pyrrolidin-1-yloxy)-4-oxo-3-(2-propenyl-penta-2,4-dienyloxycarbonyl amino)-pentanoic acid;
5-Benzoylaminooxy-3-benzyloxycarbonylamino-4-oxo-pentanoic acid;
3-Benzyloxycarbonylamino-4-oxo-5-(3-phenyl-propionyl-aminooxy)-pentanoic acid;
3-Benzyloxycarbonylamino-5-(2-naphthalen-1-yl-acetyl-aminooxy)-4-oxo-pentanoic acid;
3-Benzyloxycarbonylamino-5-(3-naphthalen-1-yl-propionylaminooxy)-4-oxo-pentanoic acid;
3-Benzyloxycarbonylamino-5-[methyl-(3-phenyl-propionyl)-aminooxy]-4-oxo-pentanoic acid;
5-(Benzoyl-methyl-aminooxy)-3-benzyloxycarbonylamino-4-oxo-pentanoic acid;
3-Benzyloxycarbonylamino-5-[methyl-(3-naphthalen-1-yl-propionyl)-aminooxy]-4-oxo-pentanoic acid;
3-Benzyloxycarbonylamino-5-[methyl-(naphthalen-1-yl-acetyl)-aminooxy]-4-oxo-pentanoic acid;
3-Benzyloxycarbonylamino-5-[benzyl-(3-phenyl-propionyl)-aminooxy3-4-oxo-pentanoic acid;
5-[Benzyl-(3-naphthalen-1-yl-propionyl)-aminooxy]-3-benzyloxycarbonylamino-4-21-pentanoic acid;
5-(3-Benzyl-2-oxo-pyrrolidin-1-yloxy)-4-oxo-3-(2-propenyl-penta-2,4-dienyloxycarbonylamino)-pentanoic acid;
5-(3-Methyl-2-oxo-pyrrolidin-1-yloxy)-4-oxo-3-(2-propenyl-penta-2,4-dienyloxycarbonylamino)-pentanoic acid;
3-Benzyloxycarbonylamino-4-oxo-5-[methyl-(phenylacetyl)-aminooxy]-pentanoic acid; or
3-Benzyloxycarbonylamino-4-oxo-5-(1-oxo-1,3-dihydro-isoindol-2-yloxy)-pentanoic acid.

Also provided is a method of inhibiting interleukin-1β converting enzyme, the method comprising administering to a patient in need of inhibition of interleukin-1β converting enzyme a therapeutically effective amount of a compound of Formula I or II.

Also provided is a method of treating or preventing stroke, the method comprising administering to a patient having a stroke or having had a stroke a therapeutically effective amount of a compound of Formula I or II.

Also provided is a method of treating inflammatory diseases, the method comprising administering to a patient having an inflammatory disease a therapeutically effective amount of a compound of Formula I or II.

In a preferred embodiment, the inflammatory disease is arthritis.

In a preferred embodiment, the inflammatory disease inflammatory bowel disease.

Also provided is a method of treating septic shock, the method comprising administering to a patient septic shock a therapeutically effective amount of a compound of Formula I or II.

Also provided is a method of treating reperfusion injury, the method comprising administering to a patient having reperfusion injury a therapeutically effective amount of a compound of Formula I or II.

Also provided is a method of treating Alzheimer's disease, the method comprising administering to a patient having Alzheimer's disease a therapeutically effective amount of a compound of Formula I or II.

Also provided is a method of treating shigellosis, the method comprising administering to a patient having shigellosis a therapeutically effective amount of a compound of Formula I or II.

Also provided is a pharmaceutically acceptable composition that contains a compound of Formula I or II.

DETAILED DESCRIPTION OF THE INVENTION

The present invention provides compounds having the Formula I

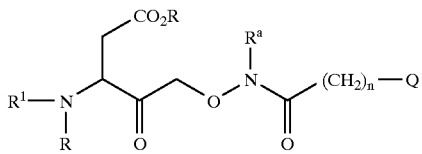

wherein
$R^1$ is

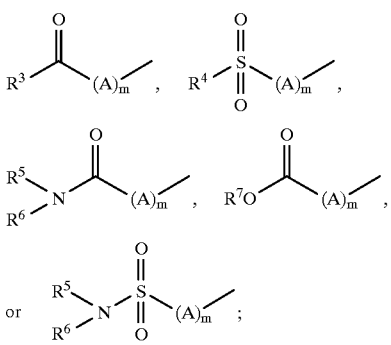

each R is independently hydrogen or $C_1$–$C_6$alkyl;
$R^3$ is hydrogen, $C_1$–$C_6$alkyl, —$(CH_2)_n$aryl, —$(CH_2)_n$heteroaryl, —$(CH_2)_p$-X-aryl, or —$(CH_2)_p$-X-heteroaryl;
$R^4$ is $C_1$–$C_6$alkyl, —$(CH_2)_n$aryl, —$(CH_2)_n$heteroaryl, —$(CH_2)_j$-X-aryl, or —$(CH_2)_j$-X-heteroaryl;
$R^5$ and $R^6$ are each independently hydrogen, $C_1$–$C_6$alkyl, —$(CH_2)_n$aryl, —$(CH_2)_n$heteroaryl, —$(CH_2)_j$-X-aryl, or —$(CH_2)_j$-X-heteroaryl;
$R^7$ is $C_1$–$C_6$alkyl, —$(CH_2)_p$aryl, —$(CH_2)_p$heteroaryl, —$(CH_2)_j$-X-aryl, or —$(CH_2)_j$-X-heteroaryl;
each n is independently 0 to 6;
each p is independently 1 to 6;
each j is independently 2 to 6;
each m is 0 to 2;
A is alanine, valine, serine, threonine, glutamic acid, lysine, arginine, histidine, glutamine, or alpha amino butyric acid;
$R^a$ is hydrogen, $C_1$–$C_6$alkyl, or —$(CH_2)_n$phenyl;

X is O or S; and
Q is $C_1$–$C_6$alkyl, —$(CH_2)_n$aryl, —$(CH_2)_n$heteroaryl, —$(CH_2)_n$heteroaryl, and the pharmaceutically acceptable salts, esters, amides, and prodrugs thereof.

In a preferred embodiment, the present invention provides compounds having the Formula II

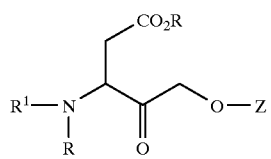

wherein Z is

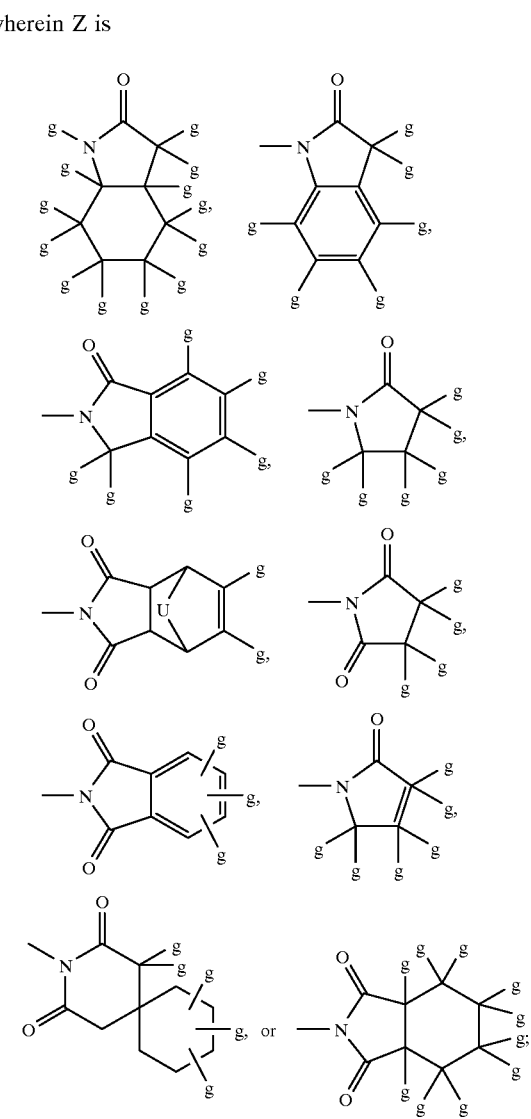

each g is independently hydrogen, $C_1$–$C_6$alkyl, $C_1$–$C_6$alkoxy, —$(CH_2)_n$$CO_2$R, —$(CH_2)_n$aryl, -aryl, —$(CH_2)_n$heteroaryl, or -heteroaryl;
U is O or $CH_2$;

$R^1$ is

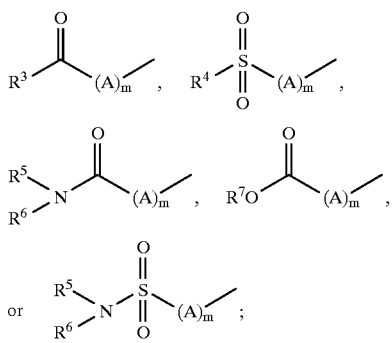

each R is independently hydrogen or $C_1$–$C_6$alkyl;

$R^3$ is hydrogen, $C_1$–$C_6$alkyl, —$(CH_2)_n$aryl, —$(CH_2)_n$heteroaryl, —$(CH_2)_p$-X-aryl, or —$(CH_2)_p$-X-heteroaryl;

$R^4$ is $C_1$–$C_6$alkyl, —$(CH_2)_n$aryl, —$(CH_2)_n$heteroaryl, —$(CH_2)_j$-X-aryl, or —$(CH_2)_j$-X-heteroaryl;

$R_5$ and $R^6$ are each independently hydrogen, $C_1$–$C_6$alkyl, —$(CH_2)_n$aryl, —$(CH_2)_n$heteroaryl, —$(CH_2)_j$-X-aryl, or —$(CH_2)_j$-X-heteroaryl;

$R^7$ is $C_1$–$C_6$alkyl, —$(CH_2)_p$aryl, —$(CH_2)_p$heteroaryl, —$(CH_2)_j$-X-aryl, or —$(CH_2)_j$-X-heteroaryl;

each n is independently 0 to 6;

each p is independently 1 to 6;

each j is independently 2 to 6;

each m is 0 to 2;

A is alanine, valine, serine, threonine, glutamic acid, lysine, arginine, histidine, glutamine, or alpha amino butyric acid; and X is O or S, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "aryl" means an aromatic hydrocarbon. Representative examples of aryl groups include phenyl, naphthyl, and biphenyl.

The term "heteroatom" includes oxygen, nitrogen, sulfur, and phosphorus.

The term "heteroaryl" means an aryl group wherein one or more carbon atom of the aromatic hydrocarbon has been replaced with a heteroatom. Examples of heteroaryl groups include furan, thiophene, pyrrole, thiazole, pyridine, pyrimidine, pyrazine, benzofuran, indole, coumarin, quinoline, isoquinoline, and naphthyridine.

The aryl or heteroaryl groups may be substituted with one or more substituents, which can be the same or different. Examples of suitable substituents include alkyl, alkoxy, thioalkoxy, hydroxy, halogen, trifluoromethyl, amino, alkylamino, dialkylamino, —$NO_2$, —CN, —$CO_2H$, —$CO_2$alkyl, —$SO_3H$, —CHO, —COalkyl, —$CONH_2$, —CONH-alkyl, —$CONHR^q$, —CON(alkyl)$_2$, —$(CH_2)_n$—$NH_2$, —$(CH_2)_n$—NH-alkyl, —$NHR^q$, or —$NHCOR^q$, where n is 1 to 5 and $R^q$ is hydrogen or alkyl. The terms "aryl" and "heteroaryl" include substituted aryl and substituted heteroaryl.

The symbol "—" means a bond.

The compounds of Formula I or II can be administered to a patient either alone or as part of a pharmaceutically acceptable composition. The compositions can be administered to patients such as humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying, and suspending agents, sweetening, flavoring, and perfuming agents.

Suspensions, in addition to the active compounds, may contain suspending agents, as for example, ethoxylated isostearyl alcohols, polyoxyethylene sorbitol, and sorbitan esters, microcrystalline cellulose, aluminum metahydroxide, bentonite, agar-agar, and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to 1,000 mg per day. For a normal human adult having a body weight of about 70 kg, a dosage in the range of about 0.01 to 100 mg per kg of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactiobionate, and laurylsulphonate salts, and the like. These may include cations based on the alkali and alkaline earth metals, such as sodium, lithium, potassium, calcium, magnesium, and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *T. Pharm Sci.*, 1977;66:1–19 which is incorporated herein by reference).

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5 or 6 membered heterocycle containing 1 nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in ,*Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention.

The compounds of the present invention can exist in different stereoisometric forms by virtue of the presence of asymmetric centers in the compounds; i.e, each asymmetric carbon can have either the R or S configuration. It is contemplated that all stereoisometric forms of the compounds as well as mixtures thereof, including racemic mixtures, form part of this invention.

The compounds of the present invention are administered to a patient in need of ICE inhibition. In general, patients in need of ICE inhibition are those patients having a disease or condition in which interleukin-1 plays a role. Examples of such diseases include, but are not limited to, inflammatory diseases such as rheumatoid arthritis and inflammatory bowel disease, neuroinflammatory disorders such as stroke, and septic shock. Other diseases include reperfusion injury, Alzheimer's disease, and shigellosis.

A "therapeutically effective amount" is an amount of a compound of Formula I or II that when administered to a patient having a disease that can be treated with a compound of Formula I or II ameliorates a symptom of the disease. A therapeutically effective amount of a compound of Formula I or II is readily determined by one skilled in the art by administering a compound of Formula I or II to a patient and observing the results.

The following examples illustrate particular embodiments of the invention and are not intended to limit the scope of the specification and claims in any manner.

EXAMPLE 1

3-Benzyloxycarbonylamino-4-oxo-5-phenylacetylaminooxy-pentanoic acid

Step A

N-(Phenylmethoxy)-benzeneacetamide [(0.760 g, 3.15 mmol), prepared by the method of Hearn M. T. W. and Ward A. D. (*Aust. J. Chem.*, 1969;22:1731)] was taken up in 10 mL of $CH_3CN$ and treated with dimethylamino-pyridine (DMAP) (50 mg) and di-tert-butyl dicarbonate (0.824 g, 3.78 mmol). The reaction was allowed to stir under Argon for 12 hours, then diluted with ethyl acetate (EtOAc) and washed with 3M $K_2S_2O_5$ (1×10 mL), $NaHCO_3$ (1×10 mL). The organic layer was dried over $Na_2SO_4$, filtered, and concentrated. Purification by chromatography ($SiO_2$, 9:1 hexane-EtOAc) afforded 0.910 g (84%) of 1,1-dimethylethyl(phenylacetyl)phenyl-methoxy) carbamate as a clear, viscous oil.

$^1$H NMR (400 MHz, DMSO-$d_6$): δ 7.41 [m, 5H], 7.32 [m, 2H], 7.24 [m, 3H], 4.90 [s, 2H], 4.09 [s, 2H], 1.48 [s, 9H]. IR (thin film) 3063, 3032, 2979, 2935, 2886, 1777, 1736, 1497, 1455, 1370, 1302 $cm^{-1}$. Mass Spectra (MS) (Chemical Ionization [CI]—$NH_3$) 342 ($M^++H$).
Elemental Analysis:
Calculated for $C_{20}H_{23}NO_4$.0.051 $CH_2Cl_2$: C, 69.66; H, 6.74; N, 4.05.
Found: C, 69.66; H. 6.83; N, 3.99.

Step B 1,1-Dimethylethyl (phenylacetyl)(phenyl-methoxy) carbamate (810 mg, 2.37 mmol) was dissolved in 75 mL of dry THF and 90 mg of 5% $PdBaSO_4$ was added. The reaction was treated with $H_2$ (20 psi) for 20 hours. The reaction was filtered through Celite and concentrated to obtain 588 mg (99%) of 1,1-dimethyl-ethyl hydroxy-(phenylacetyl) carbamate as an oil. No further purification was done.

$^1$H NMR (400 MHz, $CDCl_3$): δ 8.22 [s, 1H], 7.31 [m, 5H], 4.24 [s, 2H], 1.55 [s, 9H].

Step C (S)-5-Bromo-4-oxo-3-[[(phenylmethoxy)-carbonyl]amino]-pentanoic acid, 1,1-dimethylethyl ester [(297 mg, 0.742 mmol), prepared according to the procedure of Dolle R. E., et al., (*J. Med. Chem.*, 1994;37:563–4)], 1,1-dimethylethyl hydroxy(phenyl-acetyl) carbamate (187 mg, 0.742 mmol) and KF (104 mg, 1.85 mmol) were combined in 5 mL dimethylformamide (DMF) and allowed to stir under Ar for 12 hours. The reaction was diluted with EtOAc (15 mL) and washed with water (3×15 mL) and brine (1×15 mL). The organic layer was dried over $Na_2SO_3$ and concentrated. Purification by chromatography ($SiO_2$, 4:1 hexane-EtOAc) yielded 168 mg (40%) of [[[(1,1-dimethylethoxy)-carbonyl](phenylacetyl)amino]oxy]-4-oxo-3-[[((phenylmethoxy) carbonyl]amino]-pentanoic acid, 1,1-dimethylethyl ester as a clear oil.

$^1$H NMR (300 MHz, $CDCl_3$): δ 7.35 [m, 5H], 5.84 [d, J=9.0 Hz, 1H], 4.79, [A of AB, J=15.3 Hz, 1H], 4.70 [m, 1H], 4.57 [B of AB, J=15.3 Hz, 1H], 4.10 [s, 2H], 3.09 [dd, J=16.8, 4.6 Hz, lH], 2.79 [dd, J=16.8, 4.9 Hz, 1H], 1.52 [s, 9H], 1.39 [s, 9H]. IR (thin film) 3374, 2980, 2935, 1726 (br), 1499, 1370, 1298, 1150 $cm^{-1}$. MS (APCI, Methanol (MeOH)) 571.5 ($M^++H$).
Elemental Analysis:
Calculated for $C_{30}H_{38}N_2O_9$: C, 63.15; H, 6.71; N, 4.91.
Found: C, 62.76; H, 6.70; N, 4.69.

Step D

3-Benzyloxycarbonylamino-4-oxo-5-phenylacetylaminooxy-pentanoic acid, 1,1 dimethylethyl ester (208 mg, 0.365 mmol) was taken up in 3 mL of 1:1 trifluoroacetic acid (TFA)$CH_2Cl_2$ and allowed to stir for 2 hours. Reaction was diluted with acetonitrile (MeCN) (10 mL) and concentrated. The residue was stripped down from MeCN five times. Purification by chromatography ($SiO_2$, 90:9:1 $CH_2Cl_2$-acetone-formic acid) afforded 3-benzyloxycarbonylamino-4-oxo-5-phenylacetylaminooxy-pentanoic acid (51 mg, 34%) as a white foam.

$^1$H NMR (300 MHz, $CDCl_3$): δ 8.63 [s, 1H], 7.34 [broad (br) s, 10H], 5.48 [br d, J=4 Hz, 1H], 5.08 [br dd, J=16, 12 Hz, 2H], 4.23 [m, 1H], 3.97 [m, 2H], 3.58 [br s, 2H], 2.80 [m, 1H], 2.64 [m, 1H]. IR (KBr) 3305 (br), 2928, 1791, 1772, 1717, 1699, 1685, 1674, 1654, 1521, 1455 $cm^{-1}$. MS (APCI, MeOH) 415 ($M^++H$).
Elemental Analysis:
Calculated for $C_{21}H_{22}N_2O7$.0.106 $CF_3CO_2H$: C, 59.73; H, 5.22; N, 6.57.
Found: C, 59.73; H, 5.46; N, 6.28.

The following were prepared from (S)-5-bromo-4-oxo-3-[[(phenylmethoxy)carbonyl]amino]-pentanoic acid, 1,1-dimethylethyl ester in the manner of Example 1, Step C, and Step D.

EXAMPLE 2

3-Benzyloxycarbonylamino-4-oxo-5-(2-oxo-pyrrolidin-1-yloxy)-pentanoic acid

Step A

Prepared from 1-hydroxy-2-pyrrolidinone [Biswas A. and Miller M. J. (*Heterocycles*, 1987;26:2849)] in the manner of Example 1, Step C to give 3-benzyloxycarbonylamino-4-oxo-5-(2-oxo-pyrrolidin-1-yloxy)-pentanoic acid, 1,1-dimethylethyl ester (74%).

$^1$H NMR (400 MHz, $CDCl_3$): δ 7.37 [m, 5H]; 5.88 [br d, J=8.9 Hz]; 5.16 [A of AB, J=12.2 Hz, 1H]; 5.11 [B of AB, J=12.2 Hz, 1H]; 4.95 [A of AB, J=17.1 Hz, 1H], 4.81 [B of AB, J=17.1 Hz, 1H], 4.60 [m, 1H], 3.62 [m, 2H], 3.01 [dd, J=17.1, 4.6 Hz, 1H], 2.75 [dd, J=17.1, 4.8 Hz, 1H], 2.30 [t, J=7.95 Hz, 2H], 1.99 [quint, J=7.5 Hz, 2H], 1.41 [s, 9H]. IR (KBr) 3328 (br), 2976, 2932, 1717, 1701, 1522, 1256 $cm^{-1}$. MS (APCI, MeOH) 421 ($M^++H$).
Elemental Analysis:
Calculated for $C_{21}H_{28}N_2O_7$.0.096 DMF: C, 59.81; H, 6.76; N, 6.87.
Found: C, 59.56; H, 7.00; N, 6.52.

Step B:

Prepared from 3-benzyloxycarbonylamino-4-oxo-5-(2-oxo-pyrrolidin-1-yloxy)-pentanoic acid, 1,1-dimethylethyl ester in the manner of Example 1, Step D to afford 3-benzyloxycarbonylamino-4-oxo-5-(2-oxo-pyrrolidin-1-yloxy)-pentanoic acid (72%).

$^1$H NMR (400 MHz, $CDCl_3$): δ 8.55 [br s, 1H], 7.36 [m, 5H], 5.46 [br d, J=9.4 Hz, 1H], 5.14 [A of AB, J=5.2 Hz, 1H], 5.11 [B of AB, J=5.2 Hz, 1H], 4.23 [m, 1H], 4.19 [A of

AB, J=13.3 HZ, 1H], 3.96 [B of AB, J=13.3 Hz, 1H], 3.67 [m, 1H], 3.52 [dd, J=15.1, 7.9 Hz, 1H], 2.84 [dd, J=16.9, 8.2 Hz, 1H], 2.61 [dd, J=16.9, 10.9 HZ, 1H], 2.42 [m, 2H], 2.11 [m, 2H]. IR (KBr) 3408 (br), 2926, 1791, 1717, 1700, 1540, 1268, 1054 cm$^{-1}$. MS (APCI, MeOH) 365 (M$^+$+H).
Analysis calculated for $C_{17}H_{20}N_2O_7 \cdot 0.32\ C_3H_7OC_3H_7$: C, 57.27; H, 6.24; N, 7.04.
Found: C, 57.27; H, 6.24; N, 6.74.

EXAMPLE 3

3-Benzyloxycarbonylamino-5-(3,5-dioxo-10-oxa-4-aza-tricyclo[5.2.1.0$^{2,6}$]dec-8-en-4-yloxy )-4-oxo-pentanoic acid Step A Prepared from 3a,4,7,7a-tetrahydro-2-hydroxy-4,7-epoxy-1H-isoindole-1,3(2H)-dione [Narita M., Teramoto T, Okawara M (*Bull. Chem. Soc. Jap.*, 1971;44:1084)] in the manner of Example 1, Step C, to afford 3-benzyloxycarbonylamino-5-(3,5-dioxo-10-oxa-4-aza-tricyclo[5.2.1.0$^{2,6}$]dec-8-en-4-yloxy )-4-oxo-pentanoic acid, 1,1-dimethylethyl ester (64%). $^1$H NMR (400 MHz, DMSO-d$_6$): δ 7.84 [d, J=8.2 Hz, 1H], 7.34 [m, 5H], 6.54 [s, 2H], 5.16 [s, 2H]; 5.07 [A of AB, J=12.5 Hz, 1H], 5.03 [B of AB, J=12.5 Hz, 1H], 4.93 [A of AB, J=16.2 Hz, 1H], 4.87 [B of AB, J=16.2 Hz, 1H], 4.52 [m, 1H], 2.87 [s, 2H], 2.73 [dd, J=16.2, 5.8 Hz, 1H], 2.50 [obscured by dimethyl-sulfoxide (DMSO) resonance], 1.37 [s, 9H]. IR (KBr) 3421, 2979, 2930, 1790, 1726, 1520, 1368 cm$^{-1}$. MS (APCI, MeOH) 445 (M$^+$–C$_4$H$_8$).
Analysis calculated for $C_{25}H_{28}N_2O_9$: C, 59.65; H, 5.70; N, 5.35.
Found: C, 59.99; H, 5.64; N, 5.60.

Step B

Prepared from 3-benzyloxycarbonylamino-5-(3,5-dioxo-10-oxa-4-aza-tricyclo[5.2.1.0$^{2,6}$]dec-8-en-4-yloxy)-4-oxo-pentanoic acid, 1,1-dimethylethyl ester in the manner of Example 1, Step C to give 3-benzyloxy-carbonylamino-4-oxo-5-phenylacetylaminooxy-pentanoic acid (78%). IR (thin film) 3360, 1789, 1723, 1530, 1220 cm$^{-1}$. MS (APCI, MeOH) 445 (M$^+$+H).
Elemental Analysis:
Calculated for $C_{21}H_{20}N_2O_9 \cdot 0.194\ CF_3CO_2H$: C, 55.06; H, 4.36; N, 5.96.
Found: C, 55.06; H, 4.58; N, 5.99.

EXAMPLE 4

3-Benzyloxycarbonylamino-5-(2-oxo-2,3-dihydro-indol-1-yloxy)-4-oxo-pentannic acid Prepared from 1-hydroxyoxindole [Kende A. S. and Thurston J. (*Synthetic Communications*, 1990;20:2133–8)] to give 3-benzyloxycarbonylamino-4-oxo-5-(2-oxo-2,3-dihydro-indol-1-yloxy)-pentanoic acid (24%), mp 58–70° C. (decomposes).
Elemental Analysis:
Calculated for $C_{21}H_{20}N_2O_7$: C, 61.16; H, 4.89; N, 6.79.
Found: C, 60.84; H, 4.72; N, 6.46.

EXAMPLE 5

3-Benzyloxycarbonylamino-5-(7-methoxycarbonylmethyl-2-oxo-octahydro-indol-1-yloxy)-4-oxo-pentanoic acid Step A Hydroxylamine hydrochloride (200 mmol, 13.8 g) was dissolved in pyridine (200 mmol, 16 mL) and methanol (10 mL), and this solution was added to a mixture of cis-2-oxo-1,3-cyclo-hexanediacetic acid, dimethyl ester [(35 mmol, 8.5 g) prepared following the procedure of Grieco P. A., Noguez J. A., Masaki Y., Hiroi K., Nishizawa M., Rosowsky A., Oppenheim S., Lazarus H. *J. Med. Chem.*, 1977;20:71] in 200 mL of MeOH. To this solution NaCNBH$_4$ (30 mmol, 1.9 g) was added in portions over about 1 hour and the resulting solution was stirred at room temperature for 4 days. The reaction mixture was then concentrated to dryness, redissolved in 500 mL ethyl acetate, and washed 3×50 mL saturated NaCl, dried with Na$_2$SO$_4$, filtered, and concentrated to yield a crude solid, which was mostly desired product and pyridine. Crude octahydro-1-hydroxy-2-oxo-1H-indole-7-acetic acid, methyl ester was recrystallized from EtOAc to yield 4.05 g (51%) of a white solid.
$^1$H-NMR: 9.26 [1H, s], 3.64 [1H, dd], 3.59 [3H, s], 2.65 [1H, dd], 2.49 [1H, dd], 2.34 [1H, dd], 2.18 [1H, m], 2.04 [1H, m], 1.79, 1H, d], 1.62 [1H, m], 1.60 [1H, s-br], 1.42 [1H, m], 1.25 [2H, m], 1.06 [1H, m]. MS (CI, NH$_3$) 228 (M$^+$+H).

Step B

Prepared from octahydro-1-hydroxy-2-oxo-1H-indole-7-acetic acid, methyl ester in the manner of Example 1, Step C, to afford 3-benzyloxycarbonylamino-5-(7-methoxycarbonylmethyl-2-oxo-octahydro-indol-1-yloxy)-4-oxo-pentanoic acid, 1,1-trimethylethyl ester as a glassy oil (45%).
$^1$H NMR (400 MHz, DMSO-d$_6$, 1:1 mix of diastereomers): δ 7.85 [d, J=5.8 Hz, 0.5H], 7.83 [d, J=5.8 Hz, 0.5H], 7.35 [m, 5H], 5.06 [s, 2H], 4.94 [A of AB, J=16.9 Hz, 0.25H], 4.87 [A of AB, J=17.6 Hz, 0.25H], 4.82 [B of AB, J=17.6 HZ, 0.25H], 4.74 [B of AB=, J=16.9 Hz, 0.25H], 4.23 [m, 1H], 3.82 [m, 0.5H], 3.79 [m, 0.5H], 3.57 [s, 1.5H]; 3.57 [s, 1.5H], 2.72 [m, 0.5H], 2.70 [m, 0.5H], 2.52 [m, obscured by DMSO], 2.39 [m, 2H], 2.22 [br m, 1H], 2.10 [br m, 1H], 1.88 [br s, 0.5H], 1.84 [br s, 0.5H], 1.61 [m, 2H], 1.42 [m, 1H], 1.36 [s, 9H], 1.25 [m, 2H], 1.06 [m, 1H]. IR (thin film) 3418, 3344, 3017, 2979, 2934, 2860, 1725, 1506 cm$^{-1}$. MS (APCI, MeOH) 547.6 (M$^+$+H).

Step C

Prepared from 3-benzyloxycarbonylamino-5-(7-methoxycarbonylmethyl-2-oxo-octahydro-indol-1-yloxy)-4-oxo-pentanoic acid, 1,1-trimethylethyl ester in the manner of example 1, step D to afford 3-benzyloxycarbonylamino-5-(7-methoxycarbonylmethyl-2-oxo-octahydro-indol-1-yloxy)-4-oxo-pentanoic acid (45%), mp 55–58° C.
$^1$H NMR (400 MHz, DMSO-d$_6$, 1:1 mix of diastereomers): δ 12.4 [s, 1H], 7.84 [m, 1H], 7.35 [m, 5H], 5.05 [s, 2H], 4.86 [m, 2H], 4.45 [m, 1H], 3.83 [m, 0.5H], 2.79 [m, 0.5H], 3.59 [s, 1.5H], 3.58 [s, 0.5H], 2.57 [m, obscured by DMSO], 2.41 [complex m, 4H], 2.20 [m, 2H], 1.88 [m, 1H], 1.62 [m, 2H], 1.43 [m, 2H], 1.23 [m, 2H], 1.05 [m, 1H]. IR (KBr) 3337, 2931, 1790, 1726, 15384 cm$^{-1}$. MS (ES, NH$_4$OH) 489.5 (M$^{+-H}$).
Elemental Analysis:
Calculated for $C_{24}H_{30}N_2O_9$: C, 58.77; H, 6.16; N, 5.71.
Found: C, 59.19; H, 6.40; N, 5.34.

EXAMPLE 6

3-Benzyloxycarbonylamino-4-oxo-5-(2-oxo-octahydro-indol-1-)yloxy)-pentanoic acid Step A Ethyl 2-cyclohexanoneacetate (4.28 g, 23.3 mmol) and O-benzyl hydroxylamine hydrochloride were combined in 100 mL of ethanol (EtOH) and 2.59 g (25.6 mmol, 3.55 mL) of triethyl amine(Et$_3$N) was added. The reaction was stirred at room temperature for 12 hours at which point it was concentrated in vacuo. The residue was taken up in EtOAc and washed with 1N HCl (2×20 mL), saturated NaHCO$_3$ (1×20 mL), dried over Na$_2$SO$_4$, filtered, and concentrated. Purification by chromatography (SiO$_2$, 90:1 hexanes-EtOAc) afforded (2-benzyloxyimino-cyclohexyl)-acetic acid ethyl ester (4.76 g, 72%) as a mixture of oxime isomers.

$^1$H NMR (400 MHz, CDCl$_3$ 7:1 mixture of oxime isomers): δ 7.32 [complex m, 5H], 5.05 [s, 0.25 H], 5.02 [s, 1.H], 4.05 [q, J=7.2 Hz, 2H], 3.20 [m, 1H], 2.73 [complex m, 2H], 2.46 [d, J=8.0 Hz, 0.125H], 2.21 [dd, J=15.4, 6.3 Hz, 0.875H], 1.92 [m, 1H], 1.79 [complex m, 3H], 1.43 [m, 1H], 1.38 [complex m, 2H], 1.22 [t, J=7.2 Hz, 3H]. IR (thin film) 2931, 1735, 1638, 1451 cm$^{-1}$. MS (CI, NH$_3$) 290 (M$^+$+H). Calculated for C$_{17}$H$_{23}$N$_1$O$_3$: C, 70.56; H, 8.01; N, 4.84. Found: C, 70.47; H, 7.92; N, 4.78.

Step B (2-Benzyloxyimino-cyclohexyl)-acetic acid ethyl ester (4.66 g, 16.1 mmol) was taken up in 15 mL of acetic acid (AcOH) and NaBH$_3$CN and stirred for 72 hours. Reaction was poured into NaHCO$_3$ and extracted into EtOAc (3×30 mL). The combined organic layers were washed once with brine, dried over Na$_2$SO$_4$, filtered, and concentrated. The clear oil was dissolved in 50 mL of MeOH and K$_2$CO$_3$ (5.55 g, 40.2 mmol) was added and the reaction stirred for 12 hours. The reaction was concentrated, the residue taken up in CHCl$_3$, filtered, and concentrated. Purification by chromatography (SiO$_2$, 4:1 hexanes/EtOAc) afforded 1.72 g (43%) of cis-(2-benzyloxyamino-cyclohexyl)-acetic acid ethyl ester and 0.441 g (11%) of trans-(2-benzyloxyamino-cyclohexyl)-acetic acid ethyl ester.

Data for cis isomer:

$^1$H NMR (400 MHz, CDCl$_3$): δ 7.44 [complex m, 2H], 7.37 [complex m, 3H], 5.05 [A of AB, J=10.4 Hz, 1H], 4.94 [B of AB, J=10.4 Hz, 1H], 3.47 [dd, J=10.6, 5.3 HZ, 1H], 2.33 [dd, J=16.4 Hz, 1H], 2.20 [m, 1H], 2.08 [dd, J=16.4, 4.6 HZ, 1H], 1.74 [complex m, 2H], 1.60 [m, 1H], 1.32 [complex m, 5H]. IR (solution, CHCl$_3$) 3031, 2932, 2856, 1717, 1453 cm$^{-1}$. MS (CI, NH$_3$) 246 (M$^+$+H).

Data for trans isomer: mp 79–82° C.

Elemental Analysis:

Calculated for C$_{15}$H$_{19}$N$_1$O$_2$: C, 73.44 H, 7.81; N, 5.71. Found: C, 73.38; H, 7.89; N, 5.63.

Step C

Prepared from cis-(2-benzyloxyamino-cyclohexyl)-acetic acid ethyl ester in the manner of Example 1, Step B to give cis-1-hydroxy-octahydro-indol-2-one (85%), mp 85–86° C.

$^1$H NMR (400 MHz, CDCl$_3$): δ 9.86 [br s, 1H], 3.75 [dd, J=10.4, 4.8 Hz, 1H], 2.41 [dd, J=16.1, 7.7 Hz, 1H], 2.33 [m, 1H], 1.97 [m, 1H], 1.71 [complex m, 2H], 1.54 [m, 1H], 1.44 [complex m, 2H], 1.31 [complex m, 2H]. IR (KBr) 3037, 2936, 2856, 2710, 1690, 1659, 1548 cm$^{-1}$. MS (CI, NH$_3$) 156 (M$^+$+H)

Elemental Analysis:

Calculated for C$_8$H$_{13}$N$_1$O$_2$: C, 61.91; H, 8.44; N, 9.03. Found: C, 61.94; H, 8.49; N, 8.96.

Step D

Prepared from cis-1-hydroxy-octahydro-indol-2-one in the manner of Example 1 step C to afford 3-benzyloxycarbonylamino-4-oxo-5-(2-oxo-octahydro-indol-1-yloxy)-pentanoic acid, 1,1 dimethylethyl ester (41%). IR (thin film) 2933, 1723, 1516, 1367 cm$^{-1}$.

Elemental Analysis:

Calculated for C$_{25}$H$_{134}$N$_2$O$_7$: C, 63.28; H, 7.22; N, 5.90. Found: C, 63.03; H, 7.36; N, 5.65.

Step E

Prepared from 3-benzyloxycarbonylamino-4-oxo-5-(2-oxo-octahydro-indol-1-yloxy)-pentanoic acid, 1,1-dimethylethyl ester in the manner of Example 1, Step D to afford 3-benzyloxycarbonylamino-4-oxo-5-(2-oxo-octahydro-indol-1-yloxy)-pentanoic acid (72%). IR (KBr) 3352 (br), 2935, 2869, 1789, 1704, 1535 cm$^{-1}$. MS (APCI, MeOH) 419.5 (M$^+$+H).

Elemental Analysis:

Calculated for C$_{21}$H$_{26}$N$_2$O$_7$.0.12 H$_2$O.0.322 CH$_2$Cl$_2$: C, 57.17; H, 6.05; N, 6.26.

Found: C, 57.17; H, 6.05;N, 5.89.

The following were prepared from 5-bromo-3-[2-(2-benzyloxycarbonylamino-3-methyl-butyrylamino)-propionylamino]-)-4-oxo-pentanoic acid, 1,1-dimethyl ester [Dolle R. E., et al. (*J. Med Chem.*, 1994;37:563–4)] in the manner of Example 1, Step C and Step D.

EXAMPLE 7

3-[2-(2-Benzyloxycarbonylamino-3-methyl-butyrylamino)-propionylamino]-5-(7-methoxycarhonylmethyl-2-oxo-octahydro-indol-1-yloxy-4-oxo-pentanoic acid Prepared from octahydro-1-hydroxy-2-oxo-1H-indole-7-acetic acid, methyl ester (65%), mp 162–167° C., dec.

Elemental Analysis:

Calculated for C$_{29}$H$_{34}$N$_4$O$_9$ .0.75 H$_2$O (596.127): C, 58.43; H, 6.00; N, 9.40.

Found: C, 58.40; H, 5.68; N, 9.19.

EXAMPLE 8

3-[2-(2-benzyloxicarbonylamino-3-methyl-butyrylamino)-propionylamino]-4-oxo-5-(2-oxo-2,3-dihydro-indol-1-yloxy)-pentanoic acid Prepared from 1-hydroxyoxindole [Kende A. S. and Thurston J. (*Synthetic communications*, 1990;20:2133–8)] to afford 3-[2-(2-benzyloxycarbonylamino-3-methyl-butyrylamino)-propionylamino]-4-oxo-5-(2-oxo-2,3-dihydro-indol-1-yloxy)-pentanoic acid(67%), mp 162–167° C., dec.

Elemental Analysis:

Calculated for C$_{29}$H$_{34}$N$_4$O$_9$ .0.75 H$_2$O (596.127): C, 58.43; H, 6.00; N, 9.40.

Found: C, 58.40; H, 5.68; N, 9.19.

The following compounds were prepared using automated parallel synthesis, as follows:

To a 7-mL screw top glass vial containing 17 mg (0.3 mmol, 3 eq) of potassium fluoride was added 500 μL (0.1 mmol, 1 eq) of a 0.2M solution of the appropriate hydroxamate in DMF. The reaction vial was agitated for a few minutes and the potassium fluoride did not completely dissolve. At this point, 500 μL (0.1 mmol, 1 eq) of 0.2M solution of (S)-5-bromo-4-oxo-3-[[(phenylmethoxy) carbonyl]amino]-pentanoic acid, 1,1-dimethylethyl ester in DMF. The vials were capped and the rack of 30 to 40 vials were placed atop a circular agitator for 12 hours.

The reaction mixtures were diluted with 2 mL of ethyl acetate followed by 2 mL of deionized water. Two milliliters of liquid was withdrawn from the middle of the vial and injected rapidly back in twice. The vials were allowed to sit for 30 minutes and the organic layer was withdrawn from the upper half of the vial. Twice more, 2 mL of ethyl acetate was added, mixed, and separated. The combined organic layers were evaporated under a steady stream of nitrogen overnight.

The crude residue from the reactions were dissolved in 3 to 4 mL of 40% TFA in methylene chloride. The vials were agitated to ensure complete dissolution in a fume hood without caps. After 2 hours the vials were again placed under a steady stream of nitrogen overnight.

The crude reaction mixture was taken up in 1 mL of chloroform (MeOH was sometimes added to complete dissolution). The solutions were applied to 500-μ preparative silica gel TLC plates and then eluted with 20% acetone in methylene chloride with 1% to 2% acetic acid. The product bands were visualized by UV absorption, scraped from the plate, and the silica gel washed with methanol into a tared vial. The vials were placed under a stream of nitrogen overnight. The weighed purified products were then diluted to 10 mM in 25% methanol in chloroform and aliquoted to plates for both analytical analysis and biological evaluation. The solutions were allowed to evaporate in the fume hood over 72 hours.

EXAMPLE 9

3-Benzyloxycarbonylamino-5-(2,5-dioxo-pyrrolidin-1-)yloxy)-4-oxo-pentannic acid

EXAMPLE 10

3-Benzyloxycarbonylamino-4-oxo-5-(2,2,3-trimethyl-5-oxo-pyrrolidin-1-)yloxy)-pentanoic acid

EXAMPLE 11

3-Benzyloxycarbonylamino-5-(1,3-dioxo-octahydro-isoindol-2-yloxy)-4-oxo-pentanoic acid

EXAMPLE 12

3-Benzyloxycarbonylamino-5-(1,3-dioxo-1,3-dihydro-isoindol-2-yloxy)-4-oxo-pentanoic acid

EXAMPLE 13

3-Benzyloxycarbonylamino-5-[3-(4-bromo-phenyl)-2,5-dioxo-2,5-dihydro-pyrrol-1-yloxy]-4-oxo-pentanoic acid

EXAMPLE 14

3-Benzyloxycarbonylamino-5-(3,5-dixo-4-aza-tricyclo-[5,2,1,02.6]dec-8-en-4-yloxy)-4-oxo-pentanoic acid

EXAMPLE 15

3-Benzyloxycarbonylamino-5-(2,4-dioxo-3-aza-spiro[5,5]-undec-3-ylcoxy)-4-oxo-pentanoic acid

EXAMPLE 16

5-(2-Biphenyl-4-yl-5-oxo-pyrrolidin-1-yloxy-4-oxo-3-(2-propenyl-penta-2,4-dienyloxycarbonylamino)-pentanoic acid

EXAMPLE 17

5-Benzoylaminooxy-3-benzyloxycarbonylamino-4-oxo-pentanoic acid

EXAMPLE 18

3-Benzyloxycarbonylamino-4-oxo-5-(3-phenyl-propionylaminooxy)-pentanoic acid

EXAMPLE 19

3-Benzyloxycarbonylamino-5-(2-naphthalen-1-yl-acetylaminooxy)-4-oxo-pentanoic acid

EXAMPLE 20

3-Benzyloxycarbonylamino-5-(3-naphthalen-1-yl-propionylaminooxy)-4-oxo-pentanoic acid

EXAMPLE 21

3-Benzyloxycarbonylamino-5-[methyl-(3-phenyl-propionyl)-aminooxy]-4-oxo-pentanoic acid

EXAMPLE 22

5-(Benzoyl-methyl-aminooxy)-3-benzyloxycarbonylamino-4-oxo-pentanoic acid

EXAMPLE 23

Benzyloxycarbonylamino-5-[methyl-(3-naphthalen-1-yl-propionyl)-aminooxy]-4-oxo-pentannoic acid

EXAMPLE 24

3-Benzyloxycarbonylamino-5-[methyl-(naphthalen-1-yl-acetyl)-aminooxy]-4-oxo-pentanoic acid

EXAMPLE 25

3-Benzyloxycarbonylamino-5-[benzyl-(3-phenyl-propionyl)-aminooxy]-4-oxo-pentanoic acid

EXAMPLE 26

5-Benzyl-(3-naphthalen-1-yl-propionyl)-aminooxyl-3-benzyloxycarbonylamino-4-21-pentanoic acid

EXAMPLE 27

5-(3-Benzyl-2-oxo-pyrrol idin-1-yl oxy -4-oxo-3-(2-propenyl-penta-2,4-dienyloxycarhonylamino)-pentanoic acid

EXAMPLE 28

5-(3-Methyl-2-oxo-pyrrolidin-1-yloxy)-4-oxo-3-(2-propenyl-penta-2,4-dienyloxycarbonylamino)-pentanoic acid

EXAMPLE 29

3-Benzyloxycarbonylamino-4-oxo-5-[methyl-(phenyl-acetyl)-aminooxy]-pentanoic acid

INHIBITION STUDIES

Compounds of Formulas I and II are inhibitors of ICE as demonstrated by measurement of $K_i$ ($\mu$M) and $IC_{50}$ ($\mu$M)

using the protocol described herein. ICE (0.24 nM final concentration) is added to 400 μL of HGDE buffer (100 mM HEPES, 20% glycerol, 5 mM DTT, 0.5 mM EDTA) containing 15 μM substrate (Ac-Tyr-Val-Ala-Asp-AMC; $K_M$=15 μM) plus vehicle (DMSO) or inhibitor at concentrations bracketing the $K_i$. Substrate hydrolysis is monitored for 300 seconds by observing the fluorescence of released AMC using excitation at 380 nm and emission at 460 nm. Mean rates of substrate hydrolysis are evaluated by linear-regression analysis of the fluorescence vs time traces. To evaluate $K_i$, plots of percent inhibition vs inhibitor concentration are fit by non-linear regression to a reversible, competitive model:

$$\% \text{ Inhibition} = \frac{100 * [I]}{[I] + K_i * \left(1 + \frac{[S]}{K_M}\right)}$$

where the competition factor (1+[S]/KM)=2.

ICE Colorimetric Dose-Response ($IC_{50}$) Assay

Diluted inhibitor stocks are prepared by two-fold serial dilution from a primary stock whose concentration is selected (based on screening results or on prior attempts at $IC_{50}$ evaluation) to achieve approximately 95% inhibition in the most concentrated well. Aliquots of each dilution are transferred to a microtitre plate in triplicate.

ICE enzyme is diluted to approximately 24 nM in HGE buffer (100 mM Hepes pH 7.5, 0.5 mM EDTA, 20% glycerol, 0.1% Bovine Serum Albumin (BSA), and activated by adding dithiothreitol (DTT) to a final concentration of 5 mM. The activated enzyme is then aliquoted into wells containing inhibitor or vehicle, and the plate is preincubated for 60 minutes at ambient temperature. Substrate (Ac-Tyr-Val-Ala-Asp-pNA) is added to each well to a final concentration of 50 μM, and plates are placed in the microtitre plate-reader thermostated to 25° C. Beginning 5 minutes after addition of substrate, absorbance (405 nm) of wells is monitored for 1 hour, and activity is calculated as the mean rate of change in absorbance during this interval.

Further evidence that compounds of Formula I are inhibitors of ICE is provided by their ability to inhibit IL-1β production in human peripheral blood mononuclear cells (PBMCs) as described herein. PBMCs are isolated from heparinized blood by centrifugation over a ficoll cushion, then washed three times with phosphate-buffered saline. PBMCs are suspended in a medium containing RPMI 1640 with glutamine, penicillin, streptomycin and 2% human AB serum, then plated at $10^6$ cells per well in 96 well flat bottom plates. PBMCs are stimulated overnight with 10 ngmL of lipopolysaccharide (LPS, *E. coli* strain 0111:B4; Calbiochem) in the presence or absence of a compound of Formulas I or II. Medium is harvested and the level of mature IL-1β was determined using an ELISA kit from R & D Systems. Cells were cultured for an additional 4 hours in the presence of 3-(4,5-dimethylthiazol-2-yl)-2,5-diphenyltetrazolium bromide (MTT) to determine viability.

Ich-2 Colorimetric Dose-Response ($IC_{50}$Assay

Inhibition of Ich-2 enzyme is assayed as described above for ICE, except that enzyme is used at 64 nM, and 60 μM of the Ich-2-specific substrate Ac-Leu-Glu-Val-Asp-pNA is used instead of the ICE substrate Ac-Tyr-Val-Ala-Asp-pNA.

The results of these tests are shown below in Table 1.

TABLE 1

| Example Number | ICE $K_i$ (μM) | ICE $IC_{50}$ | PBMC $IC_{50}$ (μM) | PBMC $TC_{50}$ (μM) | Ich-2 $IC_{50}$ (μM) |
|---|---|---|---|---|---|
| 1 | 79 | 260 | 817 | | |
| 2 | 87 | 397 | | | |
| 3 | 2.1 | 0.46 | 1000 | 1000 | .100 |
| 4 | 1.6 | 3.1 | 1000 | 1000 | .079 |
| 5 | 15 | 80 | 883 | | 34 |
| 6 | 9.2 | 37 | | | |
| 7 | 0.007 | 0.026 | 4.8 | | .140 |
| 8 | 0.002 | 0.003 | 3.0 | | .005 |

HEPES = 4-(2-hydroxymethyl)-1-piperazine ethane sulfonic acid
DTT = Dithiothreitol
EDTA = Ethylene diamine tetra acetic acid
AMC = 7-amino-4-methyl coumarin
Ac = Acetyl
Tyr = Tyrosine
Val = Valine
Ala = Alanine
Asp = Aspartic Acid
Abu = Alpha amino butyric acid
pNA = Para nitroaniline
LEU = Leucine
Glu = Glutamic acid

We claim:

1. A compound having the Formula II

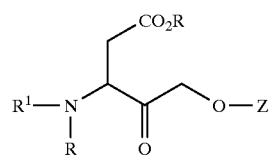

wherein Z is

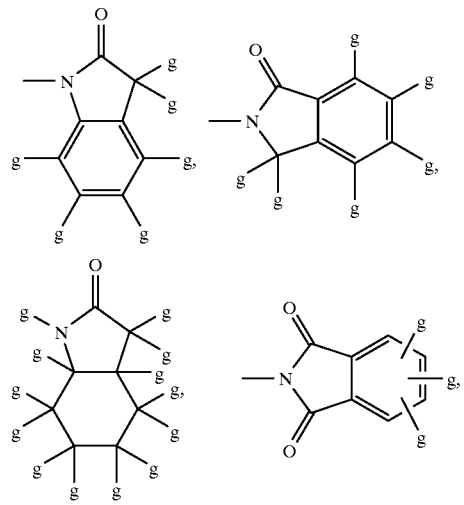

-continued

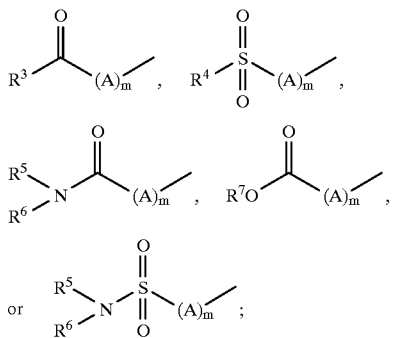

each g is independently hydrogen $C_1$–$C_6$alkyl, $C_1$–$C_6$alkoxy, —$(CH_2)_nCO_2R$, —$(CH_2)_n$aryl, -aryl, —$(CH_2)_n$heteroaryl, or -heteroaryl;

U is O or $CH_2$;

$R^1$ is

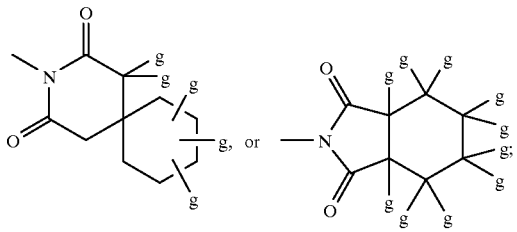

each R is independently hydrogen or $C_1$–$C_6$alkyl;

$R^3$ is hydrogen, $C_1$–$C_6$alkyl, —$(CH_2)_n$aryl, —$(CH_{2n}$heteroaryl, —$(CH_2)_p$-X-aryl, or —$(CH_2)_p$-X-heteroaryl;

$R^4$ is $C_1$–$C_6$alkyl, —$(CH_2)_n$aryl, —$(CH_2)_n$heteroaryl, —$(CH_2)_j$-X-aryl, or —$(CH_2)_j$-X-heteroaryl;

$R^5$ and $R^6$ are each independently hydrogen, $C_1$—$C_6$alkyl, —$(CH_2)_n$aryl, —$(CH_2)_n$heteroaryl, —$(CH_2)_j$-X-aryl, or —$(CH_2)_j$-X-heteroaryl;

$R^7$ is $C_1$–$C_6$alkyl, —$(CH_2)_p$aryl, —$(CH_2)_p$heteroaryl, —$(CH_2)_j$-X-aryl, or —$(CH_2)_j$-X-heteroaryl;

each n is independently 0 to 6;

each p is independently 1 to 6;

each j is independently 2 to 6;

each m is 0 to 2;

A is alanine, valine, serine, threonine, glutamic acid, lysine, arginine, histidine, glutamine, or alpha amino butyric acid;

X is O or S, and the pharmaceutically acceptable salts, esters, aramides, and prodrugs thereof.

2. A compound according to claim 1 wherein $R^1$ is

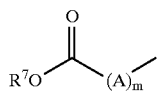

and m is 0.

3. A compound according to claim 1 wherein $R^1$ is

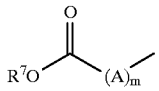

m is 0, and $R^7$ is —$(CH_2)_n$-aryl.

4. A compound according to claim 1 wherein $R^7$ is —$(CH_2)_n$-phenyl.

5. A compound according to claim 1 wherein Z is

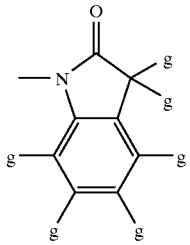

and each g is hydrogen.

6. The compounds:
[3-Benzyloxycarbonylamino-4-oxo-5-phenylacetylaminooxy-pentanoic acid;
3-Benzyloxycarbonylamnino-4-oxo-5-(2-oxo-pyrrolidin-1-yloxy)-pentanoic acid;
3-Benzyloxycarbonylamino-5-(3,5-dioxo-10-oxa-4-aza-tricyclo[5.2.1.0$^{2,6}$]dec-8-en-4-yloxy-4-oxo-pentanoic acid;]
3-Benzyloxycarbonylamino-5-(2-oxo-2,3-dihydro-indol-1-yloxy)-4-oxo-pentanoic acid;
3-Benzyloxycarbonylamino-5-(7-methoxycarbonylmethyl-2-oxo-octahydro-indol-1-yloxy)-4-oxo-pentanoic acid;
3-Benzyloxycarbonylamino-4-oxo-5-(2-oxo-octahydro-indol-1-yloxy)-pentanoic acid;
3-[2-(2-Benzyloxycarbonylamino-3-methyl-butyrylamino)-propionylamino]-5-(7-methoxycarbonylmethyl-2-oxo-octahydro-indol-1-yloxy)-4-oxo-pentanoic acid;
3-[2-(2-benzyloxycarbonylamino-3-methyl-butyrylamino)-propionylamino]-4-oxo-5-(2-oxo-2,3-dihydro-indol-1-yloxy)-pentanoic acid,
[3-Benzyloxycarbonylamino-5-(2,5-dioxo-pyrrolidin-1-yloxy)-4-oxo-pentanoic acid;
3-Benzyloxycarbonylamino-4-oxo-5-(2,2,3-trimethyl-5-oxo-pyrrolidin-1-yloxy)-pentanoic acid;]
3-Benzyloxycarbonylamino-5-(1,3-dioxo-octahydro-isoindol-2-yloxy)-4-oxo-pentanoic acid;
3-Benzyloxycarbonylamino-5-(1,3-dioxo-1,3-dihydro-isoindolyl-2-yloxy)-4-oxo-pentanoic acid;
[3-Benzyloxycarbonylamino-5-[3-(4-bromo-phenyl)-2,5-dioxo-2,5-dihydro-pyrrol-1-yloxy]-4-oxo-pentanoic acid;
3-Benzyloxycarbonylamino-5-(3,5-dioxo-4-aza-tricyclo[5.2.1.0$^{2,6}$]dec-8-en-4-yloxy)-4-oxo-pentanoic acid;]
3-Benzyloxycarbonylamino-5-(2,4-dioxo-3-aza-spiro[5.5]undec-3-yloxy)-4-oxo-pentanoic acid;
[5-(2-Biphenyl-4-yl-5-oxo-pyrrolidin-1-yloxy)-4-oxo-3-(2-propenyl-penta-2,4-dienyloxycarbonyl amino)-pentanoic acid,
5-Benzoylaminooxy-3-benzyloxycarbonylamino-4-oxo-pentanoic acid;
3-Benzyloxycarbonylamino-4-oxo-5-(3-phenyl-propionylaminooxy)-pentanoic acid;
3-Benzyloxycarbonylamino-5-(2-naphthalen-1-yl-acetylaminooxy)-4-oxo-pentanoic acid;

3-Benzyloxycarbonylamino-5-(3-naphthalen-1-yl-propionylaminooxy)-4-oxo-pentanoic acid;

3-Benzyloxycarbonylarnino-5-[methyl-(3-phenyl-propionyl)-aminooxy]-4-oxo-pentanoic acid;

5-(Benzoyl-methyl-aminooxy)-3-benzyloxycarbonyl-amino-4-oxo-pentanoic acid;

3-Benzyloxycarbonylamino-5-[methyl-(3-naphthalen-1-yl-propionyl)-aminooxy]-4-oxo-pentanoic acid;

3-Benzyloxycarbonylamino-5-[methyl-(naphthalen-1-yl-acetyl)-aminooxy]-4-oxo-pentanoic acid;

3-Benzyloxycarbonylamino-5-[benzyl-(3-phenyl-propionyl)-aminooxy]-4-oxo-pentanoic acid;

5-[Benzyl-(3-naphthalen-1-yl-propionyl)-aminooxy]-3-benzyloxycarbonylaamino-4-oxo-pentanoic acid;

5-(3-Benzyl-2-oxo-pyrrolidin-1-yloxy)-4-oxo-3-(2-propenyl-penta-2,4-dienyloxycarbonylamino)-pentanoic acid;

5-(3-Methyl-2-oxo-pyrrolidin-1-yloxy)-4-oxo-3-(2-propenyl-penta-2,4-dienyloxycarbonylamino)-pentanoic acid;

3-Benzyloxycarbonylamino-4-oxo-5-[methyl-(phenylacetyl)-aminooxy]-pentanoic acid; and] or 3-Benzyloxycarbonylamino-4-oxo-5-(1-oxo-1,3-dihydro-isoindolyl-2-yloxy)-pentanoic acid.

7. A method of inhibiting interleukin-1β converting enzyme, the method comprising administering to a patient in need of inhibition of interleukin-1β, converting enzyme a therapeutically effective amount of a compound of claim 1.

8. A method of treating or preventing stroke, the method comprising administering to a patient having a stroke or having had a stroke a therapeutically effective amount of a compound of claim 1.

9. A method of treating inflammatory diseases, the method comprising administering to a patient having an inflammatory disease a therapeutically effective amount of a compound of claim 1.

10. The method of claim 9 wherein the inflammatory disease is arthritis.

11. The method of claim 9 wherein the inflammatory disease inflammatory bowel disease.

12. A method of treating septic shock, the method comprising administering to a patient having septic shock a therapeutically effective amount of a compound of claim 1.

13. A method of treating reperfusion injury, the method of comprising administering to a patient having reperfusion injury a therapeutically effective amount of a compound of claim 1.

14. A method of treating Alzheimer's disease, the method comprising administering to a patient having Alzheimer's disease a therapeutically effective amount of a compound of claim 1.

15. A method of treating shigellosis, the method comprising administering to a patient having shigellosis a therapeutically effective amount of a compound of claim 1.

16. A pharmaceutically acceptable composition that comprises a compound of claim 1 and a pharmaceutically acceptable diluent, carrier or excipient.

* * * * *